United States Patent [19]
Chen

[11] Patent Number: 5,123,908
[45] Date of Patent: Jun. 23, 1992

[54] ANASTOMOTIC DEVICE

[76] Inventor: Fusen H. Chen, 12 Vernon La., Thompson, Conn. 06277

[21] Appl. No.: 735,950

[22] Filed: Jul. 25, 1991

Related U.S. Application Data

[63] Continuation-in-part of Ser. No. 629,608, Dec. 18, 1990, Pat. No. 5,089,008, which is a continuation-in-part of Ser. No. 472,209, Jan. 26, 1990, Pat. No. 4,997,439, which is a continuation-in-part of Ser. No. 303,326, Jan. 26, 1989, Pat. No. 4,930,502.

[51] Int. Cl.$^5$ .................................................. A61B 17/00
[52] U.S. Cl. ...................................... 606/153; 606/154
[58] Field of Search .................................. 606/153, 154

[56] References Cited

U.S. PATENT DOCUMENTS

| | | | |
|---|---|---|---|
| 2,638,901 | 5/1953 | Sugarbaker | 606/153 |
| 3,990,434 | 11/1976 | Free | 606/153 |
| 4,523,592 | 6/1985 | Daniel | 606/153 |
| 4,693,249 | 9/1987 | Schenck et al. | 606/153 |
| 4,747,407 | 5/1988 | Liu et al. | 606/153 |

FOREIGN PATENT DOCUMENTS 7400096  7/1975  Netherlands ......................... 606/153

Primary Examiner—Stephen C. Pellegrino
Assistant Examiner—Gary Jackson
Attorney, Agent, or Firm—Morris Kaplan

[57] ABSTRACT

An anastomotic device of a pair of telescopically and frictionally locked annuli which each have a plurality of spaced retaining pins that each project from an inner wall of the annuli and are adapted to pierce a lumen wall to be joined, extend axially withiun said lumen wall and into the body of the opposed lumen wall.

6 Claims, 1 Drawing Sheet

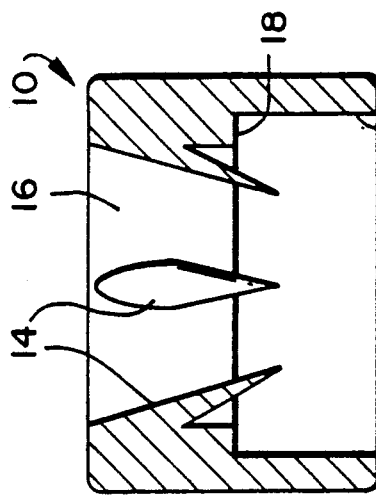
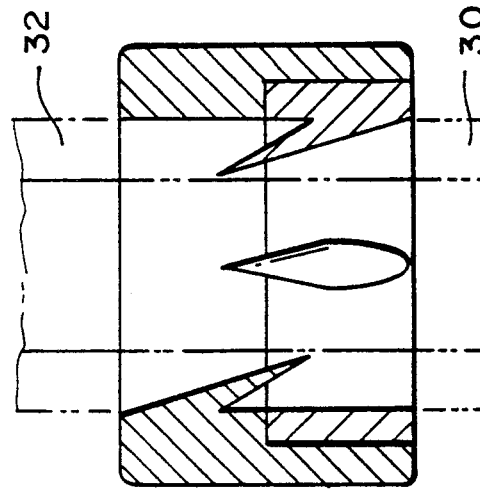
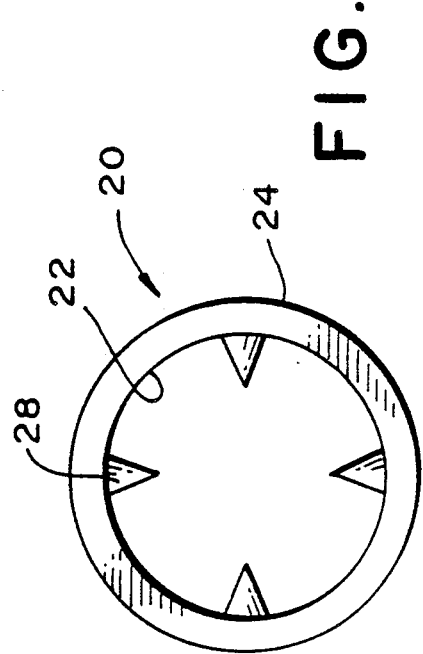
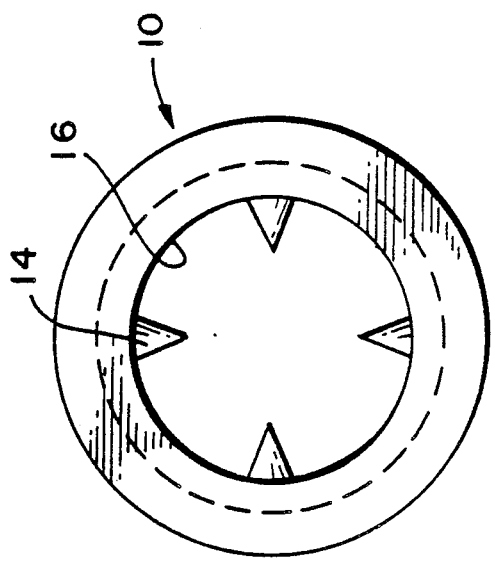
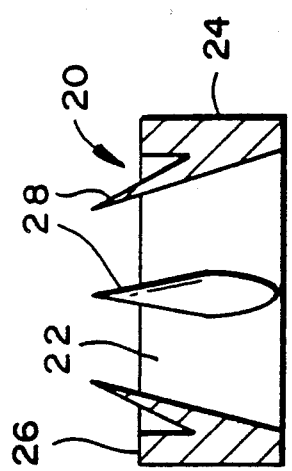

ANASTOMOTIC DEVICE

CROSS-REFERENCE TO RELATED APPLICATIONS

This application is a continuation-in-part of application Ser. No. 07/629,608, filed Dec. 18, 1990, now U.S. Pat. No. 5,089,008, which is a continuation-in-part of application Ser. No. 07/472,209, filed Jan. 26, 1990, now U.S. Pat. No. 4,997,439, which, in turn, is a continuation-in-part of application Ser. No. 07/303,326, filed Jan. 26, 1989, now U.S. Pat. No. 4,930,502.

TECHNICAL FIELD

The present invention relates to the surgical joining of tubular structures.

BACKGROUND OF THE INVENTION

The use of anastomotic devices for clamping and suturing is well known in the medical art. See, for instance, U.S. Pat. Nos. 2,638,901 (Sugarbaker); 3,254,650 (Collito); 4,233,981 (Schomacher); 4,294,255 (Geroc); 4,523,592 (Daniel); 4,657,019 (Walsh et al.); 4,747,407 (Liu et al.); and 4,757,407 (Liv et al.).

These patents are discussed in part in the referenced parent application files, the disclosures of which applications are incorporated herein by reference.

Prior art devices of the type are not fully satisfactory for at least some of the reasons that:

the device comprises a clamping means that requires a relatively large contact area with the tissue or body structure;

the device requires eversion of, and clamping pressure on, the anastomosed parts that may be causative of necrosis or at least result in severely diminished blood flow and a prolonged period for healing;

the device is of undue size and weight;

the device is awkward to use, in contradistinction to efficient surgical procedure; and the device is relatively sophisticated with respect to manufacture and use.

SUMMARY OF THE INVENTION

The present invention is directed to an improved surgical device that is: mechanically simple and inexpensive to manufacture; easy to use to thus facilitate efficient surgical procedure; provides for minimal device-to-body structure area of contact; provides a telescopic-friction-interlock of annular parts which results in a simplified structure of reduced mass and which parts are each provided with spaced retaining pins that are each adapted to effect anastomosis by impaling a respective first lumen wall, extend therethrough in the luminal axis direction and subsequently impale an opposed lumen wall to effect surgical joinder.

BRIEF DESCRIPTION OF THE DRAWINGS

FIG. 1 is an elevational sectional view of the outer annulus of the device.

FIG. 2 is a top-plan view of the outer annulus.

FIG. 3 is a elevational sectional view of the inner annulus.

FIG. 4 is a plan view of the inner annulus.

FIG. 5 is an elevational view of the device in operative association of its parts and functional with respect to anastomosed structure shown in broken lines; parts of retaining pins being omitted for clarify.

DETAILED DESCRIPTION OF THE INVENTION

Referring to the drawings which illustrate a preferred embodiment of the invention and wherein like numerals indicate like elements of structure, there is shown in FIGS. 1-2 an annular member 10 having an inner wall portion 12 of diminished thickness and a series of spaced retaining pins 14 that each project inwardly from the outer end portion of wall section 16 of said inner wall and extend further into the annular member to beyond the shoulder 18 that terminates the diminished wall portion 12.

FIGS. 3-4 disclose an annular member 20 having an inner wall 22, an outer wall 24, and an end wall 26.

As shown in FIG. 5, member 20 is dimensioned to be telescopically received and frictionally locked in annulus 10, with said end wall 26 abutting shoulder 18 and the inner surfaces 16, 22 presenting in effect a continuous wall of generally uniform diameter; but for said retaining pins 14 and corresponding pins 28 that are integral with annulus 20, project inwardly from an end section of inner wall 22 and extend beyond the transverse plane of mating of said end wall 26 and shoulder 18.

FIG. 5 further discloses the novel and improved device in functional relationship with anastomosed lumens 30, 32 (shown in broken lines), whose intima are opposed and aligned. For purposes of clarity, not all retainer pin structure is disclosed, and the parts are dimensionally exaggerated.

In use, the annuli are arranged for operative association so that the axially opposed retaining pins are in alternate relationship with one another, and a separate lumen wall is inserted into a respective one of the annuli and then retracted to effect impalement on the associated retaining pins to the extent that each lumen wall end associates and aligns with its respective end wall 18 or 26. As shown, the retaining pins lie within the respective lumen walls except for end portions which extend through the respective ends of the lumen walls and are adapted to extend into and within the opposed lumen wall. The annuli are then telescopically joined whereby to be frictionally locked and the free ends of the retaining pins entered into the opposed lumen. Means may be provided to either visually or mechanically effect such alternate disposition of the retaining pins.

The retaining pins may vary in configuration with a view to enhancing lumen retention, and the number of pins utilized may vary in accordance with specific need and, but for the least diameter inner wall part, the stepped wall configuration may comprise mechanical choice only.

The materials of fabrication are flexible, compatible with that of the human body and, where practical, are preferably absorbable and may be treated or coated in order to control the time of material dissolution, as is known in the art.

The anastomotic embodiment of the invention described and illustrated is of relative small mass, simplistic in structure and mechanical association, is significantly of minimal radial extension and, in use, requires no lumen eversion or distortion.

The embodiment shown and described is only illustrative of the present invention and is not to be construed as delimitive thereof; since once apprised of the invention, changes in structure would be readily apparent to one skilled in the art. Hence, the present invention includes all modifications of the structure encompassed within the spirit and scope of the following claims.

I claim:

1. Means for joining tubular elements, especially an anastomotic device, comprising:
   first and second annular members;
   said first member (20) being configured to be telescopically received, in frictional retention, within a diminished wall thickness portion (12) of the second (10) of said members;
   said diminished wall thickness portion (12) extending axially from one end of said member (10);
   the inner walls of said members in such telescopic assembly presenting a generally continuous inner wall (16, 22) of generally uniform diameter; and
   pin means integral with and extending from said inner wall and disposed within said assembly of annular members for retaining said tubular elements in a joined relationship.

2. Means as in claim 1, wherein:
   said retaining pin means comprise a first plurality (14) of spaced pins that each projects inwardly from the inner wall of the second member, at the outer end section removed from the diminished wall thickness portion (12), and extends to beyond the transverse plane of mating of the inner walls of said first and second members; and
   each of said pins is dimensioned and configured to pierce a first body of said joined tubular elements, extend in general axial direction within the wall of said first tubular element and into the body of the opposed second tubular element.

3. Means as in claim 2, wherein:
   said retaining means further comprise a second plurality (28) of spaced relationship pins that dimensionally and configuratively correspond to said first plurality of pins; and
   each pin of said second plurality projects inwardly from the inner wall of the first annular member (20), at an end section removed from that end to be aforesaid telescopically received, and extends to beyond said transverse plane of mating;
   whereby each pin of said second plurality is adapted to pierce the body of said second tubular element, extend generally axially within the wall of said second element and onto the body of the opposed first tubular element.

4. Means as in claim 3, wherein the assembled annuli, each pin of each said plurality lies intermediate pins of the opposed plurality of pins.

5. Means as in claim 1, wherein the inner wall of said diminished wall thickness portion terminates at a shoulder (18) configuration and the telescopically received end (26) of said first member abuts said shoulder.

6. Means as in claim 5, wherein:
   said retaining means comprise a first plurality of spaced pins, each said pin projecting inwardly from an outer end section of the inner wall of said first member and extending to beyond the transverse plane of mating of the inner walls of said first and second members;
   each said first plurality of pins being dimensioned and configured to pierce a first body of said tubular elements to be joined, extend in general axial direction within the wall of said first tubular part and into the body of the opposed second tubular element to be joined; and
   said retaining means further comprise a second plurality of spaced pins that dimensionally and configuratively correspond to said first plurality of pins, each said second plurality of pins projects inwardly from an outer end section of the inner wall of the second annular member and extends to beyond said transverse plane of mating,
   whereby each pin of said second plurality is adapted to pierce the body of said second tubular element, extend generally axially within the wall of said second element and into the body of the opposed first tubular element.

* * * * *